US006495662B1

(12) United States Patent
Gardella et al.

(10) Patent No.: US 6,495,662 B1
(45) Date of Patent: Dec. 17, 2002

(54) BIOACTIVE PEPTIDES AND PEPTIDE DERIVATIVES OF PARATHYROID HORMONE (PTH) AND PARATHYROID HORMONE-RELATED PEPTIDE (PTHRP)

(75) Inventors: Thomas J. Gardella, Needham; Henry M. Kronenberg, Belmont; John T. Potts, Jr., Newton; Harald Jüppner, Cambridge, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/421,379

(22) Filed: Oct. 20, 1999

Related U.S. Application Data

(60) Provisional application No. 60/105,530, filed on Oct. 22, 1998.

(51) Int. Cl.⁷ .......................... C07K 5/00; A01N 37/18; A61K 38/00
(52) U.S. Cl. ............................. 530/300; 514/2
(58) Field of Search ............... 530/317; 514/2, 514/44

(56) References Cited

U.S. PATENT DOCUMENTS

| | | | | |
|---|---|---|---|---|
| 4,698,328 | A | | 10/1987 | Neer et al. ............... 514/12 |
| 4,761,406 | A | | 8/1988 | Flora et al. ............... 514/86 |
| 5,217,896 | A | * | 6/1993 | Kramer et al. ......... 435/240.27 |
| 5,556,940 | A | * | 9/1996 | Willick et al. .............. 530/317 |
| 5,717,062 | A | * | 2/1998 | Chorev et al. .............. 530/317 |
| 6,066,618 | A | | 5/2000 | Holick ...................... 514/12 |

FOREIGN PATENT DOCUMENTS

| | | |
|---|---|---|
| CA | 2126132 | 12/1995 |
| EP | 0 783 522 B1 | 12/2001 |
| WO | WO 91/05050 | 4/1991 |
| WO | WO 98/05683 | 2/1998 |

OTHER PUBLICATIONS

Ding et al., A single amino acid determines the immunostimulatory activity of interleukin 10, Jan. 2000, J. Exp. Med., vol. 191 No. 2 pp. 213–223.*

Verma et al., Gene therapy—promises, problems and prospects, Sep. 1997, Nature, vol. 389 pp. 239–242.*

Orkin et al, Report and recommendations of the panel to assess the NIH investment in research on gene therapy, Dec. 1995, NIH, pp. 1–39.* www.molecularprobes.com, Jan. 2001, Molecular Probes.* www.radioparm.com, Jan. 2001, Dupont Pharmaceuticals.*

Abou–Samra, A.–B. et al., "Non–homologous sequences of parathyroid hormone related peptide bind to a common receptor on ROS 17/2.8 Cells," *Endocrinology* 125:2215–2217 (1989).

Azarani, A. et al., "Structurally diverse N–terminal peptides of parathyroid hormone (PTH) and PTH–related peptide (PTHRP) inhibit the Na⁺/H⁺exchanger NHE3 isoform by binding to the PTH/PTHRP receptor type I and activating distinct signaling pathways," *J. Biol. Chem.* 271:14931–14936 (1996).

Born, W. et al., "Inhibition of parathyroid hormone bioactivity by human parathyroid hormone (PTH)–(3–84) and PTH–(8–84) synthesized in *Escherichia coli*," *Endocrinol.* 123:1848–1853 (1988).

Caulfield, M.P. et al., "The bovine renal parathyroid hormone (PTH) receptor has equal affinity for two different amino acid sequences: The receptor binding domains of PTH and PTH–related protein are located within the 14–34 region," *Endocrinology* 127:83–87 (1990).

Dempster, D.W. et al., "Anabolic actions of parathyroid hormone on bone," *Endocrine Reviews* 14:690–709 (1993).

Dempster, D.W. et al., published corrections to "Anabolic actions of parathyroid hormone on bone," Endocrine Review 14:690–709 (1993), *Endocrine Review* 15:261 (1994).

Fairwell, T. et al., "Total solid–phase synthesis, purification, and characterization of human parathyroid hormone–(1–84)," *Biochemistry* 22:2691–2697 (1983).

Gardella, T.J. et al., "Analysis of parathyroid hormone's principal receptor–binding region by site–directed mutagenesis and analog design," *Endocrinology* 132:2024–2030 (1993).

Gardella, T.J. et al.,"Mutational analysis of the receptor–activating region of human parathyroid hormone," *J. Biol. Chem.* 266:13141–13146 (1991).

Goltzmann, D. et al., "Analysis of the requirements for the parathyroid hormone action in renal membranes with the use of inhibiting analogues," *J. Biol. Chem.* 250:3199–3203 (1975).

Goud, N.A. et al., "Solid–phase synthesis and biologic activity of human parathyroid hormone(1–84)," *Journal of Bone and Mineral Research* 6: 781–789 (1991).

(List continued on next page.)

*Primary Examiner*—Deborah J. Reynolds
*Assistant Examiner*—Eleanor Sorbello
(74) *Attorney, Agent, or Firm*—Sterne, Kessler, Goldstein & Fox PLLC

(57) ABSTRACT

Novel parathyroid hormone peptide (PTH) and parathyroid hormone related peptide (PTHrP) or derivatives thereof which are biologically active are disclosed, as are pharmaceutical compositions containing said peptides, and synthetic and recombinant methods for producing said peptides. Also disclosed are methods for treating mammalian conditions characterized by decreases in bone mass using therapeutically effective pharmaceutical compositions containing said peptides. Also disclosed are methods for screening candidate compounds of the invention for antagonistic or agonistic effects on parathyroid hormone receptor action. Also disclosed are diagnostic and therapeutic methods of said compounds.

16 Claims, 5 Drawing Sheets

OTHER PUBLICATIONS

Horiuchi, N. et al., "A parathyroid hormone inhibitor in vivo: Design and biological evaluation of a hormone analog," *Science* 220:1053–1055 (1983).

Juppner, H. et al., "The parathyroid hormone–like peptide associated with humoral hypercalcemia of malignancy and parathyroid hormone bind to the same receptor on the plasma membrane of ROS 17/2.8 cells," *J. Biol. Chem.* 263:8557–8560 (1988).

Kimura, T. et al., "Strategy for the synthesis of large peptides: an application to the total synthesis of human parathyroid hormone [hPTH(1–84)]," *Biopolymers* 20:1823–1832 (1981).

Nussbaum, S.R. et al., "Parathyroid hormone•renal receptor interactions," *J. Biol. Chem.* 255:10183–10187 (1980).

Rixon, R.H. et al., "Parathyroid hormone fragments may stimulate bone growth in ovariectomized rats by activating adenylyl cyclase," *Journal of Bone and Mineral Research* 9:1179–1189 (1994).

Rosenblatt, M., "Parathyroid Hormone: Chemistry and Structure–Activity Relations," in *Pathobiology Annual*, Ioachim, H.L., ed., Raven Press, New York, pp. 53–86 (1981).

Shen, V. et al., "Effects of combined and separate intermittent administration of low–dose human parathyroid hormone fragment (1–34) and 17β–estradiol on bone histomorphometry in ovariectomized rats with established osteopenia," *Calcif. Tissue Int.* 50:214–220 (1992).

Slovik, D.M. et al., "Restoration of spinal bone in osteoporotic men by treatment with human parathyroid hormone (1–34) and 1,25–dihydroxyvitamin D," *Journal of Bone and Mineral Research* 1:377–381 (1986).

Tregear, G.W. et al., "Bovine parathyroid hormone: Minimum chain length of synthetic peptide required for biological activity," *Endodcrinol.* 93:1349–1353 (1973).

Whitfield, J.F. et al., "Comparison of the ability of recombinant human parathyroid hormone, rhPTH–(1–84), and hPTH–(1–31)$NH_2$ to stimulate femoral trabecular bone growth in ovariectomized rats," *Calcif. Tissue Int.* 60:26–29 (1997).

Whitfield, J.F. et al., "Restoration of severely depleted femoral trabecular bone in ovariectomized rats by parathyroid hormone–(1–34)," *Calcif. Tissue Int.* 56:227–231 (1995).

Whitfield, J.F. and Morley, P., "Small bone–building fragments of parathyroid hormone: new therapeutic agents for osteoporosis," *TiPS* 16:382–386 (1995).

Whitfield, J.F. et al., "Stimulation of the growth of femoral trabecular bone in ovariectomized rats by the novel parathyroid hormone fragment, hPTH–(1–31)$NH_2$ (Ostabolin)," *Calcif. Tissue Int.* 58:81–87 (1996).

Bergwitz, C. et al., "Full Activation of Chimeric Receptors by Hybrids between Parathyroid Hormone and Calcitonin," *J. Biol. Chem.* 271:26469–26472 (1996).

Kemp. B.E. et al., "Parathyroid Hormone–Related Protein of Malignancy: Active Synthetic Fragments," *Science* 238:1568–1570 (1987).

Musso, M.–J. et al., "Renal vasodilatation and microvessel adenylate cyclase stimulation by synthetic parathyroid hormone–like protein fragments," *Eur. J. Pharmacol.* 174:139–151 (1989).

Tregear, G.W. et al., "Bovine Parathyroid Hormone: Minimum Chain Length of Synthetic Peptide Required for Biological Activity," *Endocrinol.* 93:1349–1353 (1973).

Takasu, H. et al., "Human PTH/PTHrP receptors and Type–2 PTH Receptors Show Discordant Selectivity for Human PTH Analogs with Amino–Terminal Modifications," *Bone* 23:s255, Abstract No. T223 (Nov. 1998).

Takasu, H. et al., "Phospholipase C Activation via the Human PTH/PTHrP Receptor Requires an Intact Amino–Terminus of the Human PTH," *Bone* 23:S447, Abstract No. F148 (Nov. 1998).

Takasu, H. et al., "Amino–Terminal Modifications of Human Parathyroid Hormone (PTH) Selectively Alter Phospholipase C Signaling via the Type 1 PTH Receptor: Implications for Design of Signal–Specific PTH Ligands," *Biochem.* 38:13453–13460 (Oct. 1999).

International Search Report for International Application No. PCT/US/24481 filed Oct. 20, 1999.

English language translation of European Patent No. EP 0 783 522 B1 (Document AL1), Ralph McElroy Translation Company (Dec. 2001).

* cited by examiner

BIOACTIVE PEPTIDES AND PEPTIDE DERIVATIVES OF PARATHYROID HORMONE (PTH) AND PARATHYROID HORMONE-RELATED PEPTIDE (PTHRP)

This application claims the benefit of the filing date of provisional application 60/105,530 filed on Oct. 22, 1998, which is herein incorporated by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention relates to novel parathyroid hormone peptide (PTH) derivatives and to novel parathyroid hormone-related peptide (PTHrP) derivatives. In particular, the invention relates to PTH and PTHrP minimized peptide and derivatives thereof that still retain biological activity.

2. Description of Related Art

Parathyroid hormone (PTH) is a major regulator of calcium homeostasis whose principal target cells occur in bone and kidney. Regulation of calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone indirectly by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH exerts these effects primarily through receptor-mediated activation of adenylate cyclase and phospholipase C.

Disruption of calcium homeostasis may produce many clinical disorders (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a lesion (e.g., adenoma, hyperplasia, or carcinoma) of the parathyroid glands. Another type of hypercalcemia, humoral hypercalcemia ofmalignancy (HHM) is the most common paraneoplastic syndrome. It appears to result in most instances from the production by tumors (e.g., squamous, renal, ovarian, or bladder carcinomas) of a class of protein hormone which shares amino acid homology with PTH. These PTH-related proteins (PTHrP) appear to mimic certain of the renal and skeletal actions of PTH and are believed to interact with the PTH receptor in these tissues. PTHrP is normally found at low levels in many tissues, including keratinocytes, brain, pituitary, parathyroid, adrenal cortex, medulla, fetal liver, osteoblast-like cells, and lactating mammary tissues. In many HHM malignancies, PTHrP is found in the circulatory system at high levels, thereby producing the elevated calcium levels associated with HHM.

The pharmacological profiles of PTH and PTHrP are nearly identical in most in vitro assay systems, and elevated blood levels of PTH (i.e., primary hyperparathyroidism) or PTHrP (i. e., HHM) have comparable effects on mineral ion homeostasis (Broadus, A. E. & Stewart, A. F., "Parathyroid hormone-related protein: Structure, processing and physiological actions," in Basic and Clinical Concepts, Bilzikian, J. P. et al., eds., Raven Press, New York (1994), pp.259–294; Kronenberg, H. M. et al., "*Parathyroid hormone: Biosynthesis, secretion, chemistry and action*," in Handbook of Experimental Pharmacology, Mundy, G. R. & Martin, T. J., eds., Springer-Verlag, Heidelberg (1993), pp. 185–201). The similarities in the biological activities of the two ligands can be explained by their interaction with a common receptor, the PTH/PTHrP receptor, which is expressed abundantly in bone and kidney (Urena, P. et al., *Endocrinology* 134:451–456 (1994)).

Native human parathyroid hormone is an unmodified polypeptide of 84 amino acids. It is secreted from the parathyroid glands in response to low blood calcium levels and acts on osteoblast (bone-building cells) in bone, and on tubular epithelial cells of kidney. The hormone interacts with a cell surface receptor molecule, called the PTH-1 receptor or PTH/PTHrP receptor, which is expressed by both osteoblast and renal tubular cells. PTHrP, the major cause of the humoral hypercalcemia of malignancy, also has normal functions that include roles in development. PTHrP has 141 amino acids, though variants also occur that result from alternative gene splicing mechanisms. PTHrP plays a key role in the formation of the skeleton through a process that also involves binding to the PTH-1 receptor (Karaplis, A. C., et al., *Genes and Dev.* 8:277–289 (1994) and Lanske, B., et al., *Science* 273:663–666 (1996)).

The PTH-1 receptor is homologous in primary structure to a number of other receptors that bind peptide hormones, such as secretin (Ishihara, T. et al., *EMBO J.* 10:1635–1641 (1991)), calcitonin (Lin, H. Y. et al., *Science* 254:1022–1024 (1991)) and glucagon (Jelinek, L. J. et al., *Science* 259:1614–1616 (1993)); together these receptors form a distinct family called receptor family B (Kolakowski, L. F., *Receptors and Channels* 2:1–7 (1994)). Within this family, the PTH-1 receptor is unique, in that it binds two peptide ligands and thereby regulates two separate biological processes. A recently identified PTH receptor subtype, called the PTH-2 receptor, binds PTH but not PTHrP (Usdin, T., et al., *J. Biol. Chem.* 270:15455–15458(1995)). This observation implied that structural differences in the PTH and PTHrP ligands determined selectivity for interaction with the PTH-2 receptor. The PTH-2 receptor has been detected by RNA methods in the brain, pancreas and vasculature, however, its biological function has not been determined (Usdin, T., et al., *J. Biol. Chem.* 270:15455–15458 (1995)). It is hypothesized that the family B receptors use a common molecular mechanism to engage their own cognate peptide hormone (Bergwitz, C., et al., *J. Biol. Chem.* 271:26469–26472 (1996)).

The binding of either radio labeled PTH(1–34) or PTHrP (1–36) to the PTH-1 receptor is competitively inhibited by either unlabeled ligand (Jüppner, H. et al., *J. Biol. Chem.* 263:8557–8560 (1988); Nissenson, R. A. et al., *J. Biol. Chem.* 263:12866–12871 (1988)). Thus, the recognition sites for the two ligands in the PTH-1 receptor probably overlap. In both PTH and PTHrP, the 15–34 region contains the principal determinants for binding to the PTH-1 receptor. Although these regions show only minimal sequence homology (only 3 amino acid identities), each 15–34 peptide can block the binding of either PTH(1–34) or PTHrP(1–34) to the PTH-1 receptor (Nussbaum, S. R. et al., *J. Biol. Chem.* 255:10183–10187 (1980); Caulfield, M. P. et al., *Endocrinology* 127:83–87 (1990); Abou-Samra, A.-B. et al., *Endocrinology* 125:2215–2217 (1989)). Further, the amino terminal portion of each ligand is required for bioactivity, and these probably interact with the PTH-1 receptor in similar ways, since 8 of 13 of these residues are identical in PTH and PTHrP.

Both PTH and PTHrP bind to the PTH-1 receptor with affinity in the nM range; the ligand-occupied receptor transmits a "signal" across the cell membrane to intracellular effector enzymes through a mechanism that involves intermediary heterotrimeric GTP-binding proteins (G proteins). The primary intracellular effector enzyme activated by the PTH-1 receptor in response to PTH or PTHrP is adenylyl cyclase (AC). Thus, PTH induces a robust increase in the "second messenger" molecule, cyclic adenosine monophosphate (cAMP) which goes on to regulate the poorly characterized "downstream" cellular processes involved in bone-remodeling (both bone formation and bone resorption processes). In certain cell-based assay systems, PTH can stimulate effector enzymes other than AC, including phospholipase C (PLC), which results in production of inositol triphosphate ($IP_3$), diacylglycerol (DAG) and intracellular calcium ($iCa^{2+}$). The roles of these non-cAMP second messenger molecules in bone metabolism are presently unknown.

Osteoporosis is a potentially crippling skeletal disease observed in a substantial portion of the senior adult population, in pregnant women and even in juveniles. The disease is marked by diminished bone mass, decreased bone mineral density (BMD), decreased bone strength and an increased risk of bone fracture. At present, there is no effective cure for osteoporosis, though estrogen, calcitonin and the bisphosphonates, etidronate and alendronate are used to treat the disease with varying levels of success through their action to decrease bone resorption. Since parathyroid hormone regulates blood calcium and the phosphate levels, and has potent anabolic (bone-forming) effects on the skeleton, in animals (Shen, V., e al., *Calcif Tissue Int.* 50:214–220 (1992); Whitefild, J. F., et al., *Calcif Tissue Int.* 56:227–231 (1995) and Whitfield, J. F., et al., *Calcif. Tissue Int.* 60:26–29 (1997)) and humans (Slovik, D. M., et al., *J. Bone Miner. Res.* 1:377–381 (1986); Dempster, D. W., et al., *Endocr. Rev.* 14:690–709 (1993) and Dempster, D. W., et al., *Endocr. Rev.* 15:261 (1994)) when administered intermittently, PTH, or PTH derivatives, are prime candidates for new and effective therapies for osteoporosis.

Truncated PTH derivatives such as PTH(1–34) and PTH (1–31) are active in most assay systems and promote bone-formation (Whitefild, J.F., et al., *Calcif. Tissue Int.* 56:227–231 (1995); Whitfield, J. F., et al., *Calcif Tissue Int.* 60:26–29 (1997); Slovik, D. M., et al., *J. Bone Miner. Res.* 1:377–381 (1986); Tregear, G. W., et al., *Endocrinology* 93:1349–1353 (1973); Rixon, R. H., et al., *J. Bone Miner. Res.* 9:1179–1189 (1994); Whitfield, J. F. and Morley, P., *Trends Pharmacol. Sci.* 16:372–386 (1995) and Whitfield, J. F., et al., *Calcif. Tissue Int.* 58:81–87(1996)). Butthese peptides are still too large for efficient non-parenteral delivery and low cost. The discovery of an even smaller "minimized" version of PTH or PTHrP would be an important advance in the effort to develop new treatments for osteoporosis.

PTH and PTHrP derivatives that have amino acid substitutions or deletions in the 1–14 region usually exhibit diminished activity (Tregear, G. W., et al., *Endocrinology* 93:1349–1353 (1973); Goltzman, D., et al., *J. Biol. Chem.* 250:3199–3203 (1975); Horiuchi, N., et al., *Science* 220.1053–1055 (1983) and Gardella, T. J., et al., *J. Biol. Chem.* 266:13141–13146 (1991))

Several short $NH_2$-terminal PTH or PTHrP peptides have been investigated previously, but no activity was detected. For example, bPTH(1–12) was inactive in adenylyl cyclase assays performed in rat renal membranes (Rosenblatt, M., "Parathyroid Hormone. Chemistry and Structure-Activity Relations," in Pathobiology Annual, Ioachim, H. L., ed., Raven Press, New York (1981), pp. 53–84) and PTHrP (1–16) was inactive in AC assays performed in Chinese hamster ovary (CHO) cells expressing the cloned rat PTH-1 receptor (Azurani, A., et al., *J. Biol. Chem.* 271:14931–14936 (1996)). It has been known that residues in the 15–34 domain of PTH contribute importantly to receptor binding affinity, as the PTH(15–34) fragment binds weakly to the receptor, but this peptide does not activate AC (Naussbaum, S. R., et al., *J. Biol. Chem.* 255:10183–10187 (1980) and Gardella, T. J., et al., *Endocrinology* 132:2024–2030 (1993)).

SUMMARY OF THE INVENTION

The relatively large size of native PTH or PTHrP presents challenges to the use of these peptides as treatments for osteoporosis. In general, a protein of this size is not suitable for use as a drug, since it cannot be delivered effectively by simple methods such as nasal inhalation. Instead, injection is required, and in the case of PTH, daily, or almost daily injections would most likely be needed to achieve increases in bone formation rates. Additionally, larger peptides are technically difficult and expensive to prepare by conventional synthetic chemistry methods. Alternative methods employing recombinant DNA and cell-based expression systems are also expensive, potentially vulnerable to contamination by foreign proteins and do not circumvent the delivery problem.

Accordingly, it would be advantageous for those skilled in the art to be able to identify a small molecule analog (either peptide or non-peptide) that is based on the larger peptide and yet which still retains the desired biological activities. The activity may at first be weak relative to the intact peptide, but further optimization can lead to enhanced efficacy and potency.

The present invention relates to PTH(1–14)/PTHrP(1–14) peptides and derivatives thereof Compounds of the invention which include PTH(1–14)/PTHrP(1–14) peptides, fragments thereof, derivatives thereof, pharmaceutically acceptable salts thereof, and N- or C-derivatives thereof, are hereinafter collectively referred to as "compounds of SEQ ID NO:1 and derivatives thereof".

In detail, the invention provides synthetic and/or recombinant biologically active peptide derivatives of PTH(1–14) and PTHrP(1–14). In one specific embodiment, this invention provides a biologically active peptide at least 85% identical to a peptide consisting essentially of the formula:

(a) $X_{01}$ValSerGlu$X_{02}$GlnLeu$X_{03}$His$X_{04}$$X_{05}$GlyLys$X_{06}$ (SEQ ID NO:1);

(b) fragments thereof containing amino acids 1–9, 1–10, 1–11,1–12, or 1–13;

(c) pharmaceutically acceptable salts thereof; or (d) N- or C-derivatives thereof;

wherein:
- $X_{01}$ is Ser or Ala;
- $X_{02}$ is Ile or His;
- $X_{03}$ is Met, Leu or Nle;
- $X_{04}$ is Asn or Asp;
- $X_{05}$ is Leu or Lys; and
- $X_{06}$ is His or Ser, provided that said peptide is not PTHrP(1–14).

In accordance with yet a further aspect of the invention, this invention also provides pharmaceutical compositions comprising
  (a) a biologically active peptide at least 85% identical to a peptide consisting essentially of the formula: SerValSerGluIleGlnLeuMetHisAsnLeu GlyLysHis (SEQ ID NO:3);
  (b) fragments thereofcontaining amino acids 1–9, 1–10, 1–11, 1–12, or 1–13;
  (c) pharmaceutically acceptable salts thereof; or
  (d) N- or C-derivatives thereof; and a pharmaceutically acceptable carrier.

In accordance with yet a further aspect of the invention, this invention also provides pharmaceutical compositions comprising
  (a) a biologically active peptide at least 85% identical to a peptide consisting essentially of the formula: AlaValSerGluHisGlnLeuLeuHisAspLys GlyLysSer (SEQ ID NO:4);
  (b) fragments thereofcontaining amino acids 1–9, 1–10, 1–11, 1–12, or 1–13;
  (c) pharmaceutically acceptable salts thereof; or
  (d) N- or C-derivatives thereof; and a pharmaceutically acceptable carrier.

In accordance with yet a further aspect of the invention, this invention provides a nucleic acid molecule consisting essentially of a polynucleotide encoding a biologically active peptide which has an amino acid sequence selected from the group consisting of:
  (a) $X_{01}$ValSerGlu$X_{02}$GlnLeu$X_{03}$His$X_{04}$$X_{05}$GlyLys$X_{06}$ (SEQ ID NO:1); or
  (b) fragments thereofcontaining amino acids 1–9, 1–10, 1–11, 1–12, or 1–13;
wherein:
- $X_{01}$ is Ser or Ala;
- $X_{02}$ is Ile or His;
- $X_{03}$ is Met, Leu or Nle;
- $X_{04}$ is Asn or Asp;
- $X_{05}$ is Leu or Lys; and
- $X_{06}$ is His or Ser,
provided that said peptide is not PTHrP(1–14).

In accordance with yet a further aspect of the invention, this invention provides a recombinant DNA molecule comprising: (1) an expression control region, said region in operable linkage with (2) a polynucleotide sequence coding for a biologically active peptide, wherein said peptide is selected from the group consisting of:
  (a) $X_{01}$ValSerGlu$X_{02}$GlnLeu$X_{03}$His$X_{04}$$X_{5}$GlyLys$X_{06}$ (SEQ ID NO:1); or
  (b) fragments thereofcontaining amino acids 1–9, 1–10, 1–11, 1–12, or 1–13;
wherein:
- $X_{01}$ is Ser or Ala;
- $X_{02}$ is Ile or His;
- $X_{03}$ is Met, Leu or Nle;
- X04 is Asn or Asp;
- $X_{05}$ is Leu or Lys; and
- $X_{06}$ is His or Ser,
provided that said peptide is not PTHrP(1–14).

In accordance with yet a further aspect of the invention, this invention provides a method for treating mammalian conditions characterized by decreases in bone mass, which method comprises administering to a subject in need thereof an effective bone mass-increasing amount of a biologically active peptide, wherein said peptide comprises an amino acid sequence at least 85% identical to a member selected from the group consisting essentially of:
  (a) $X_{01}$ValSerGlu$X_{02}$GlnLeu$X_{03}$His$X_{04}$$X_{05}$GlyLys$X_{06}$ (SEQ ID NO:1);
  (b) fragments thereofcontaining amino acids 1–9, 1–10, 1–11, 1–12, or 1–13;
  (c) pharmaceutically acceptable salts thereof; or
  (d) N- or C-derivatives thereof;
wherein:
- $X_{01}$ is Ser or Ala;
- $X_{02}$ is Ile or His;
- $X_{03}$ is Met, Leu or Nle;
- $X_{04}$ is Asn or Asp;
- $X_{05}$ is Leu or Lys; and
- $X_{06}$ is His or Ser,
provided that said peptide is not PTHrP(1–14); and a pharmaceutically acceptable carrier.

In accordance with yet a further aspect of the invention, this invention provides a method for the treatment of a patient having need of a biologically active peptide comprising administering a therapeutically effective amount of a peptide, wherein said peptide comprises an amino acid sequence at least 85% identical to a member selected from the group consisting essentially of:
  (a) a biologically active peptide consisting essentially of the formula: SerValSerGluIleGlnLeuMetHisAsnLeuGlyLysHis (SEQ ID NO:3);
  (b) fragments thereofcontaining amino acids 1–9,1–10, 1–11, 1–12, or 1–13;
  (c) N- or C-derivatives thereof; or
  (d) pharmaceutically acceptable salts thereof; and a pharmaceutically acceptable carrier.

In accordance with yet a further aspect of the invention, this invention provides a method for the treatment of a patient having need of a biologically active peptide comprising administering a therapeutically effective amount of a peptide, wherein said peptide comprises an amino acid sequence at least 85% identical to a member selected from the group consisting essentially of:
  (a) a biologically active peptide consisting essentially of the formula: AlaValSerGluHisGlnLeuLeuHisAspLysGlyLysSer (SEQ ID NO:4);
  (b) fragments thereof containing amino acids 1–9, 1–10, 1–11, 1–12, or 1–13;
  (c) N- or C-derivatives thereof, or
  (d) pharmaceutically acceptable salts thereof, and a pharmaceutically acceptable carrier.

In accordance with yet a further aspect of the invention, there is provided a method for treating a medical disorder that results from altered or excessive action of the PTH-1/PTH-2 receptor, comprising administering to a patient a therapeutically effective amount of a biologically active peptide wherein said peptide comprises an amino acid sequence at least 85% identical to a member selected from the group consisting essentially of:
  (a) $X_{01}$ValSerGlu$X_{02}$GlnLeu$X_{03}$His$X_{04}$$X_{05}$GlyLys$X_{06}$ (SEQ ID NO:1);

(b) fragments thereofcontaining amino acids 1–9, 1–10, 1–11, 1–12, or 1–13;

(c) pharmaceutically acceptable salts thereof; or (d) N- or C-derivatives thereof, wherein:

$X_{01}$ is Ser or Ala;
$X_{02}$ is Ile or His;
$X_{03}$ is Met, Leu or Nle;
$X_{04}$ is Asn or Asp;
$X_{05}$ is Leu or Lys; and
$X_{06}$ is His or Ser, provided said peptide is not PTHrP(1–14); and a pharmaceutically acceptable carrier sufficient to inhibit activation of the PTH-1/PTH-2 receptor of said patient.

In accordance with yet a further aspect of the invention, this invention also provides a method for determining rates of bone reformation, bone resorption and/or bone remodeling comprising administering to a patient an effective amount of a labeled peptide of SEQ ID NO: 1 or a derivative thereof and determining the uptake of said peptide into the bone of said patient. The peptide may be labeled with a label selected from the group consisting of: radio label, flourescent label, bioluminescent label, or chemiluminescent label. An example of a suitable radio label is $^{99m}$Tc.

In accordance with yet a further aspect of the invention, any amino-acid substitutions at positions 1–9, and more particularly those amino acid substitutions at amino acid positions 10, 11, 12, 13, and/or 14, which do not destroy the biological activity of the PTH(1–14)/PTHrP(1–14) peptide analog to antagonize or agonize the PTH-1/PTH-2 receptor (as determined by assays known to the skilled artisan and discussed below), are also included within the scope of the present invention.

DETAILED DESCRIPTION OF THE PREFERRED EMBODIMENTS

Definitions

Figure 1:
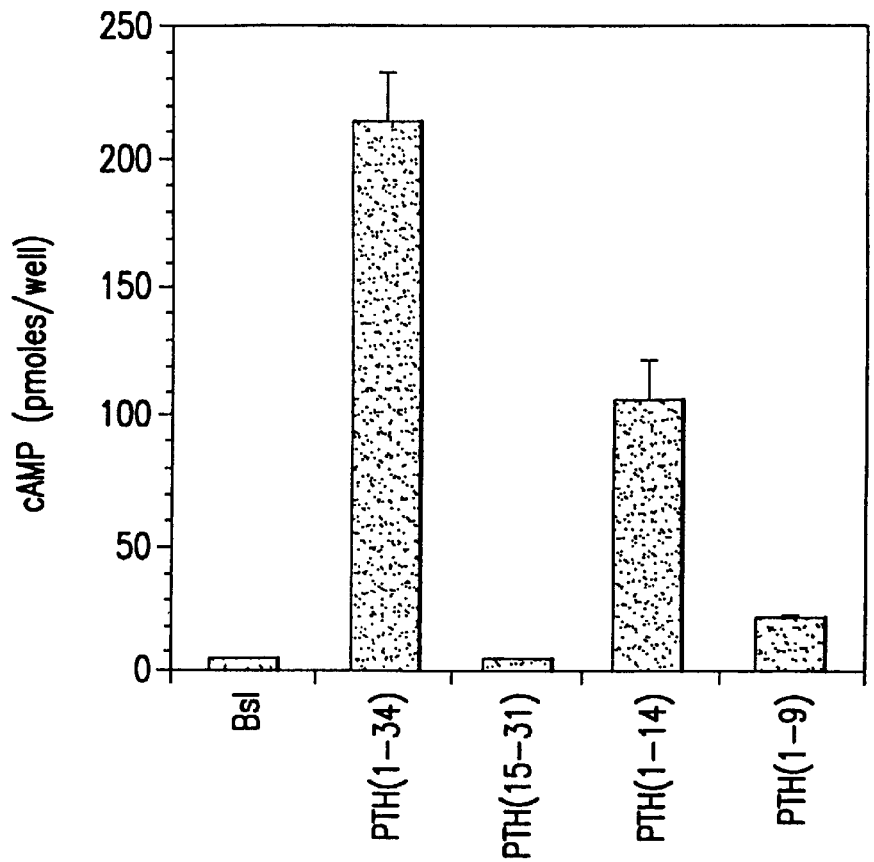
FIG. 1. Bioactivity of amino-terminal and carboxy-terminal fragments of PTH(1–34). Fragments of parathyroid hormone were synthesized by chemical methods and purified by reverse-phase HPLC. Peptides were tested for the ability to stimulate cAMP accumulation in COS-7 cells expressing the cloned human PTH-1 receptor. PTH(1–34) was tested at a dose of 1 $\mu$M, other peptides were tested at 67 $\mu$M. Peptides were tested in duplicate (±s.e.m.) at a dose of 67 $\mu$M. The cAMP in control untreated cells is indicated by Bsl. Cells were treated for 30 minutes at 21° C.

In the description that follows, a number of terms used in recombinant DNA technology and peptide synthesis are utilized extensively. In order to provide a clear and consistent understanding of the specification and claims, including the scope to be given such terms, the following definitions are provided.

Cloning vector: A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector: A vector similar to a cloning vector but which is capable of enhancing the expression of a gene which has been cloned into it, after transformation into a host. The cloned gene is usually placed under the control of (i. e., operably linked to) certain control sequences such as promoter sequences. Promoter sequences may be either constitutive or inducible.

Recombinant Host: According to the invention, a recombinant host may be any prokaryotic or eukaryotic host cell which contains the desired cloned genes on an expression vector or cloning vector. This term is also meant to include those prokaryotic or eukaryotic cells that have been genetically engineered to contain the desired gene(s) in the chromosome or genome of that organism. For examples of such hosts, see Sambrook et al., *Molecular Cloning: A Laboratory Manual*, Second Edition, Cold Spring Harbor Laboratory, Cold Spring Harbor, N.Y. (1989). Preferred recombinant hosts are eukaryotic cells transformed with the DNA construct of the invention. More specifically, mammalian cells are preferred.

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. Examples of promoters include the CMV promoter (InVitrogen, San Diego, Calif.), the SV40, MMTV, and hMTIIa promoters (U.S. Pat. No. 5,457,034), the HSV-1 4/5 promoter (U.S. Pat. No. 5,501,979), and the early intermediate HCMV promoter (WO92/17581). Also, tissue-specific enhancer elements may be employed. Additionally, such promoters may include tissue and cell-specific promoters of an organsim.

Polynucleotide: This term generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

Polypeptide: This term refers to any peptide or protein comprising two or more amino acids joined to each other by peptide bonds or modified peptide bonds, i. e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties*, 2nd Ed., T. E. Creighton, W. H. Freeman and Company, New York, 1993 and Wold, F., Posttranslational Protein Modifications: Perspectives and Prospects, pgs. 1–12 in *Posttranslational Covalent Modification of Proteins*, B. C. Johnson, Ed., Academic Press, New York, 1983; Seifter et al., "Analysis for protein modifications and nonprotein cofactors", *Methods in Enzymol*. 182:626–646 (1990) and Rattan et al., "Protein Synthesis: Posttranslational Modifications and Aging", *Ann NY Acad Sci* 663:48–62 (1992).

Homologous/Nonhomologous: Two nucleic acid molecules are considered to be "homologous" if their nucleotide sequences share a similarity of greater than 40%, as determined by HASH-coding algorithms (Wilber, W. J. and Lipman, D. J., *Proc. Natl. Acad Sci.* 80:726–730 (1983)). Two nucleic acid molecules are considered to be "nonhomologous" if their nucleotide sequences share a similarity of less than 40%.

Isolated: A term meaning altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of compounds of SEQ ID NO:1and derivatives thereof can be substantially purified by the one-step method described in Smith and Johnson, *Gene* 67:31–40 (1988).

By "isolated" is meant that the DNA is free of the coding sequences of those genes that, in the naturally-occurring genome of the organism (if any) from which the DNA of the invention is derived, immediately flank the gene encoding the DNA of the invention. The isolated DNA may be single-stranded or double-stranded, and may be genomic DNA, cDNA, recombinant hybrid DNA, or synthetic DNA. It may be identical to a native DNA sequence encoding compounds of SEQ ID NO:1 and derivatives thereof, or may differ from such sequence by the deletion, addition, or substitution of one or more nucleotides. Single-stranded DNAs of the invention are generally at least 8 nucleotides long, (preferably at least 18 nucleotides long, and more preferably at least 30 nucleotides long) ranging up to full length of the DNA molecule encoding compounds of SEQ ID NO:1 and derivatives thereof (i.e., 42 nucleotides); they preferably are detectably labeled for use as hybridization probes, and may be antisense.

High Stringency: By "high stringency" is meant, for example, conditions such as those described for the isolation of cDNA (also see Current Protocols in Molecular Biology, John Wiley & Sons, New York (1989), hereby incorporated by reference). The DNA of the invention may be incorporated into a vector [which may be provided as a purified preparation (e.g., a vector separated from the mixture of vectors which make up a library)] containing a DNA sequence encoding a peptide of the invention (e.g. compounds of SEQ ID NO:1 and derivatives thereof) and a cell or essentially homogenous population of cells (e.g., prokaryotic cells, or eukaryotic cells such as mammalian cells) which contain the vector (or the isolated DNA described above).

Identity: This term refers to a measure of the identity of nucleotide sequences or amino acid sequences. In general, the sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing. Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Preferred computer program methods to determine identity and similarity between two sequences include, but are not limited to, GCG program package (Devereux, J., et al., *Nucleic Acids Research* 12(i):387 (1984)), BLASTP, BLASTN, FASTA (Atschul, S. F., et al., *J. Molec Biol* 215:403 (1990)).

Therefore, as used herein, the term "identity" represents a comparison between a test and reference polypeptide. More specifically, reference test polypeptide is defined as any polypeptide that is 85% or more identical to a reference polypeptide. As used herein, the term at least 85% identical to refers to percent identities from 85 to 99.99 relative to the reference polypeptides. Identity at a level of 85% or more is indicative of the fact that, assuming for exemplification purposes a test and reference polynucleotide length of 100 amino acids, that no more than 15% (i.e., 15 out of 100) amino acids in the test polypeptides differ from that of the reference polypeptides. Such differences may be represented as point mutations randomly distributed over the entire length of the amino acid sequence of the invention or they may be clustered in one or more locations of varying length up to the maximum allowable 2/14 amino acid difference (approximately 85% identity). Differences are defined as amino acid substitutions, or deletions.

Fragment: A "fragment" of a molecule such as a compound of SEQ ID NO: 1 or derivative thereof is meant to refer to any polypeptide subset of these molecules.

Functional Derivative: The term "derivatives" is intended to include "variants," the "derivatives," or "chemical derivatives" of the molecule. A "variant" of a molecule such as a compound of SEQ ID NO: 1 or derivative thereof is meant to refer to a molecule substantially similar to either the entire molecule, or a fragment thereof. An "analog" of a molecule such as a compound of SEQ ID NO: 1 or derivative thereof is meant to refer to a non-natural molecule substantially similar to either the SEQ ID NO: 1 molecules or fragments thereof.

A molecule is said to be "substantially similar" to another molecule if the sequence of amino acids in both molecules is substantially the same, and if both molecules possess a similar biological activity. Thus, provided that two molecules possess a similar activity, they are considered variants, derivatives, or analogs as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Biological activity of the Protein: This expression refers to the metabolic or physiologic function of compounds of SEQ ID NO:1 or derivatives thereof including similar activities or improved activities or those activities with decreased undesirable side-effects. Also included are antigenic and immunogenic activities of said compounds of SEQ ID NO: 1 or derivatives thereof.

Fusion protein: By the term "fusion protein" is intended a fused protein comprising compounds of SEQ ID NO: 1 or derivatives thereof, either with or without a "selective cleavage site" linked at its N-terminus, which is in turn linked to an additional amino acid leader polypeptide sequence.

Selective cleavage site: The term "selective cleavage site" refers to an amino acid residue or residues which can be selectively cleaved with either chemicals or enzymes in a predictable manner. A selective enzyme cleavage site is an amino acid or a peptide sequence which is recognized and hydrolyzed by a proteolytic enzyme. Examples of such sites include, without limitation, trypsin or chymotrypsin cleavage sites.

Leader Sequence: By the term "leader sequence" is intended a polynucleotide sequence linked to compounds of SEQ ID NO: 1, and expressed in host cells as a fusion protein fused to the selective cleavage site and compounds of SEQ ID NO: 1. The term "leader polypeptide" describes the expressed form of the "leader sequence" as obtained in the fusion protein.

The fusion protein, which is often insoluble and found in inclusion bodies when it is overexpressed, is purified from other bacterial protein by methods well known in the art. In a preferred embodiment, the insoluble fusion protein is centrifuged and washed after cell lysis, and resolubilized with guanidine-HCl. It can remain soluble after removal of the denaturant by dialysis. (For purification of refractile proteins, see Jones, U.S. Pat. No. 4,512922; Olson, U.S. Pat. No. 4,518,526; and Builder et al., U.S. Pat. Nos. 4,511,502 and 4,620,948).

The recombinantly produced compounds of SEQ ID NO: 1 or derivatives thereof can be purified to be substantially free of natural contaminants from the solubilized fusion protein through the use of any of a variety of methodologies. As used herein, a compound is said to be "substantially free of natural contaminants" if it has been substantially purified from materials with which it is found following expression in bacterial or eukaryotic host cells. Compounds of SEQ ID NO: 1 or derivatives thereof may be purified through application of standard chromatographic separation technology.

Alternatively, the peptide may be purified using immuno-affinity chromatography (Rotman, A. et al., *Biochim. Biophys. Acta* 641:114–121 (1981); Sairam, M. R. J,. *Chromatog* 215:143–152 (1981); Nielsen, L. S. et al., *Biochemistry* 21:6410–6415 (1982); Vockley, J. et al., *Biochem. J.* 217:535–542 (1984); Paucha, E. et al., *J. Virol.* 51:670–681 (1984); and Chong, P. et al., *J. Virol. Meth.* 10:261–268 (1985)).

After partial or substantial purification, the fusion protein is treated enzymatically with the enzyme corresponding to the cleavage site. Alternatively, the fusion protein in its more impure state, even in refractile form, can be treated with the enzyme. If needed, the resulting mature compounds of SEQ ID NO: 1or derivatives thereof, can be further purified. Conditions for enzymatic treatment are known to those of skill in the art.

Gene Therapy: A means of therapy directed to altering the normal pattern of gene expression of an organism. Generally, a recombinant polynucleotide is introduced into cells or tissues of the organism to effect a change in gene expression.

Host Animal: Transgenic animals, all of whose germ and somatic cells contain the DNA construct of the invention. Such transgenic animals are in general vertebrates. Preferred host animals are mammals such as non-human primates, mice, sheep, pigs, cattle, goats, guinea pigs, rodents, e.g. rats, and the like. The term Host Animal also includes animals in all stages of development, including embryonic and fetal stages.

I. Compounds of SEQ ID NO: 1 and Derivatives Thereof—Structural and Functional Properties We describe herein a novel "minimized" variant of PTH that retains bioactivity, and is small enough to be deliverable by simple non-injection methods. The new peptide corresponds to the 1–14 sequence of native PTH or shorter variants thereof and thus has a molecular weight of less than 2,000 daltons. The present invention pertains to the native PTH(1–14) peptide, the 1–14 sequence of PTH-related peptide (PTHrP), and peptide derivatives derived from these peptides by alteration in amino acid composition or amino acid chain length.

The primary amino acid sequence of the native PTH (1–14) peptide (N-terminus to C-terminus) is SerValSerGluIleGlnLeuMetHisAsnLeuGlyLysHis (SEQ ID NO: 3), whereas the primary amino acid sequence of the native PTHrP(1–14) peptide (N-terminus to C-terrninus) is Ala-ValSerGluHisGlnLeuLeu HisAspLysGlyLysSer (SEQ ID NO: 4). Accordingly, the peptide sequence in common between Sequence ID NOs: 3 and 4 consists of the following generic formula:

$X_{01}$ValSerGlu$X_{02}$GlnLeu$X_{03}$His$X_{04}$$X_{05}$GlyLys$X_{06}$(SEQ ID NO:1) wherein:
$X_{01}$ is Ser or Ala;
$X_{02}$ is Ile or His;
$X_{03}$ is Met, Leu, or Nle;
$X_{04}$ is Asn or Asp;
$X_{05}$ is Leu or Lys; and
$X_{06}$ is His or Ser,
provided that said peptide is not PTHrP(1–14).

Thus, based upon the above noted generic formula, this invention provides biologically active compounds of SEQ ID NO: 1 and derivatives thereof. In one specific embodiment, this invention provides a biologically active peptide at least 85% identical to a peptide consisting essentially of the formula:

(a) $X_{01}$ValSerGlu$X_{02}$GlnLeu$X_{03}$His$X_{04}$$X_{05}$GlyLys$X_{06}$ (SEQ ID NO:1);
(b) fragments thereofcontaining amino acids 1–9, 1–10, 1–11, 1–12, or 1–13;
(c) pharmaceutically acceptable salts thereof; or
(d) N- or C-derivatives thereof;
wherein:
$X_{01}$ is Ser or Ala;
$X_{02}$ is Ile or His;
$X_{03}$ is Met, Leu or Nle;
$X_{04}$ is Asn or Asp;
$X_{05}$ is Leu or Lys; and
$X_{06}$ is His or Ser,
provided that said peptide is not PTHrP(1–14).

As protein products, compounds of SEQ ID NO: 1 or derivatives thereof of the present invention are amenable to production by the technique of solution- or solid-phase peptide synthesis. The solid phase peptide synthesis technique, in particular, has been successfully applied in the production of human PTH and can be used for the production of compounds of SEQ ID NO: 1 or derivatives thereof of the present invention (for guidance, see Kimura et al., supra, and see Fairwell et al., *Biochem.* 22:2691 (1983)). Success with producing human PTH on a relatively large scale has been reported by Goud et al., in *J. Bone Min. Res.* 6(8):781 (1991), incorporated herein by reference. The synthetic peptide synthesis approach generally entails the use of automated synthesizers and appropriate resin as solid phase, to which is attached the C-terminal amino acid of the desired compounds of SEQ ID NO: 1 or derivatives thereof. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of SEQ ID NO: 1 and derivatives thereof variants which incorporate amino acids that are not genetically encoded.

In a further aspect of the invention, any amino-acid substitutions at positions 1–9, and more particularly those amino acid substitutions at amino acid positions 10, 11, 12, 13, and/or 14, which do not destroy the biological activity of the PTH/PTHrP peptide analog to antagonize or agonize the PTH-1/PTH-2 receptor (as determined by assays known to the skilled artisan and discussed below), are also included within the scope of the present invention.

The synthetic analog of bovine PTH, PTH(3–34) has been recognized as a potent PTH antagonist in vitro. Variants of PTH lacking N-terminal amino acids 1–2 and 1–7, were shown to be devoid of agonist activity and capable of antagonist activity (Born, W. etal., *Endocrinol.* 23:1848–1853 (1988)). Preferred potential antagonist variants of SEQ ID NO: 1 of this invention are variants truncated at the N-terminus.

When a variant is truncated by one amino acid at the N-terminus, it is termed PTH or PTHrP(2–14), in that it lacks amino acid residue #1 but contains amino acid residues #2–14. When a variant is truncated by one amino acid at the C-terminus, it is termed PTH or PTHrP(1–13), in that it lacks amino acid residue #14 but contains amino acid residues #1–13.

In accordance with another aspect of the present invention, substituents may be attached to the free amine of the N-terminal amino acid of compounds of SEQ ID NO: 1 or derivatives thereof by standard methods known in the art. For example, alkyl groups, e.g., $C_{1-12}$ alkyl, may be attached using reductive alkylation. Hydroxyalkyl groups, e.g. $C_{1-12}$ hydroxyalkyl, may also be attached using reductive alkylation wherein the free hydroxy group is protected with a t-butyl ester. Acyl groups, e.g., $COE_1$, may be attached by coupling the free acid, e.g., $E_1COOH$, to the free amino of the N-terminal amino acid. Also contemplated within the scope of this invention are those compounds of SEQ ID NO:1 and derivatives thereof that alter secondary or tertiary structure, or stability of compounds of SEQ ID NO: 1 or derivatives thereof which still retain biological activity. Such derivatives might be achieved through lactam cyclization, disulfide bonds, or other means known to a person of ordinary skill in the art.

Among the preferred embodiments are those compounds which may serve as agonists of the PTH-1/PTH-2 receptor. In particular, preferred embodiments are those compounds where $X_{01}$ is Ala; $X_{02}$ is Ile; $X_{03}$ is Met; $X_{04}$ is Asn; $X_{05}$ is Leu; and $X_{06}$ is His. The amino acid sequence of this preferred embodiment is thus AlaValSerGluIleGlnLeuMetHisAsnLeuGlyLysHis (SEQ ID NO: 5) or derivatives thereof.

Another set of the preferred embodiments are those compounds having a five amino acid deletion at the carboxy terminus of SEQ ID NO: 1 where $X_{01}$ is Ala; $X_{02}$ is Ile; and $X_{03}$ is Met. The amino acid sequence of this preferred embodiment is thus AlaValSerGluIleGlnLeuMetHis (SEQ ID NO: 6) or derivatives thereof.

Another set of preferred embodiments are those compounds where $X_{01}$ is Ala; $X_{02}$ is Ile; $X_{03}$ is Leu; $X_{04}$ is Asp; $X_{05}$ is Lys; and $X_{06}$ is Ser. The amino acid sequence of this preferred embodiment is thus AlaValSerGluIleGlnLeuLeuHisAsp LysGlyLysSer (SEQ ID NO: 2) or derivatives thereof.

Another set of preferred embodiments are those compounds having a five amino acid deletion at the carboxy terminus of SEQ ID NO: 1 where $X_{01}$ is Ala; $X_{02}$ is Ile; and X03 is Leu. The amino acid sequence of this preferred embodiment is thus AlaValSerGluIleGlnLeuLeuHis (SEQ ID NO: 7) or derivatives thereof.

Another set of preferred embodiments are those compounds having a five amino acid deletion at the carboxy terminus of SEQ ID NO: 1 where $X_{01}$ is Ala; $X_{02}$ is His; and $X_{03}$ is Leu. The amino acid sequence of this preferred embodiment is thus AlaValSerGluHisGlnLeuLeuHis (SEQ ID NO: 8) or derivatives thereof.

Another set of the preferred embodiments are those compounds where $X_{01}$ is Ser; $X_{02}$ is His; X03 is Leu; $X_{04}$ is Asp; $X_{05}$ is Lys; and $X_{06}$ is Ser. The amino acid sequence of this preferred embodiment is thus SerValSerGluHisGlnLeu LeuHisAspLysGlyLysSer (SEQ ID NO: 9) or derivatives thereof.

Another set of the preferred embodiments are those compounds having a five amino acid deletion at the carboxy terminus of SEQ ID NO: 1 where $X_{01}$ is Ser; $X_{02}$ is His; and $X_{03}$ is Leu. The amino acid sequence of this preferred embodiment is thus SerValSerGluHisGlnLeuLeuHis (SEQ ID NO: 10) or derivatives thereof.

Among the preferred embodiments are those compounds which may serve as antagonists of the PTH-1/PTH-2 receptor. In particular, preferred embodiments are those compounds having a single amino acid deletion at the amino terminus of SEQ ID NO: 1 where $X_{02}$ is Ile; $X_{03}$ is Met; $X_{04}$ is Asn; X05 is Leu; and $X_{06}$ is His. The amino acid sequence of this preferred embodiment is thus ValSerGluIleGlnLeuMetHisAsnLeuGlyLysHis (SEQ ID NO: 11) or derivatives thereof.

Yet another set of preferred antagonist embodiments are those compounds having a single amino acid deletion at the amino terminus of SEQ ID NO: 1 where $X_{02}$ is Ile; $X_{03}$ is Leu; $X_{04}$ is Asp; $X_{05}$ is Lys; and $X_{06}$ is Ser. The amino acid sequence of this preferred embodiment is thus ValSerGlulleGlnLeuLeuHisAspLys GlyLysSer (SEQ ID NO: 12) or derivatives thereof.

Yet another set of preferred antagonist embodiments are those compounds having a single amino acid deletion at the amino terminus of SEQ ID NO: 1 where $X_{02}$ is His; $X_{03}$ is Leu; $X_{04}$ is Asp; $X_{05}$ is Lys; and $X_{06}$ is Ser. The amino acid sequence of this preferred embodiment is thus ValSerGluHisGlnLeuLeuHisAsp LysGlyLysSer (SEQ ID NO: 13) or derivatives thereof.

II. Biological Characterization of Compounds of SEQ ID NO:1 and Derivatives Thereof Functional characterization of the biological properties of the compounds of SEQ ID NO:1 and derivatives thereof was performed by bioassays that measure ligand-stimulated cAMP accumulation.

A. Stimulation of Cyclic AMP Accumulation by Compounds of SEQ ID NO: 1 or Derivatives Thereof Intracellular cAMP accumulation was measured as described previously (Abou-Samraetal., J. Biol. Chem. 262:1129,1986). Cells in 24-well plates were rinsed with culture medium containing 0.1% BSA and 2 mM IBMX. The cells were then incubated with compounds of SEQ ID NO: 1 or derivatives thereof for 60 min. at 21° C. The supernatant was removed and the cells immediately frozen by placing the whole plate in dry ice powder. Intracellular cAMP was extracted by thawing the cells in 1 ml of 50 mM HCl and analyzed by a specific radioimmunoassay using an anti-cAMP antibody (e.g., Sigma, St. Louis, Mo.). A cAMP analog (2'-O-monosuccinyl-adenosine 3':5'-cyclic monophosphate tyrosyl methyl ester, obtained from Sigma) which was used a tracer for cAMP was iodinated by the chloramine T method. Free iodine was removed by adsorbing the iodinated cAMP analog onto a C18 Sep-pak cartridge (Waters, Milford, Mass.). After washing with $dH_2O$, the iodinated cAMP analog was eluted from the Sep-pak Cartridge with 40% acetonitrille (ACN) and 0.1% trifluoroacetic acid (TFA). The iodinated cAMP analog was lyophilized, reconstituted in 1 ml 0.1% TFA, and injected into a C18 reverse phase HPLC column (Waters). The column was equilibrated with 10% ACN in 0.1% TFA, and eluted with gradient of 10–30% ACN in 0.1% TFA. This allows separation of the mono-iodinated cAMP analog from the non-iodinated cAMP analog. The tracer is stable for up to 4 months when stored at −20° C. The standard used for the assay, adenosine 3':5'-cyclic monophosphate, was purchased from Sigma. Samples (1–10 82 1 of HCl extracts) or standards (0.04–100 fmol/tube) were diluted in 50 mM Na-acetate (pH 5.5), and acetylated with 10 $\mu$l of mixture of triethylamine and acetic anhydride (2:1 vol:vol). After acetylation, cAMP antiserum (100 $\mu$l) was added from a stock solution (1:4000) made in PBS (pH 7.4), 5 mM EDTA and 1% normal rabbit serum. The tracer was diluted in PBS (pH 7.4) with 0. 1% BSA, and added (20,000 cpm/tube). The assay was incubated at 4° C. overnight. The bound tracer was precipitated by adding 100 μl of goat anti-rabbit antiserum (1:20 in PBS) and 1 ml of 7% polyethyleneglycol (MW 5000–6000), centrifuging at 2000 rpm for 30 min. at 4° C. The supernatant was removed and the bound radioactivity was counted in a gamma-counter (Micromedic). To compute the cAMP data, logit calculations were performed in Excel spreadsheets. Typically, the assay sensitivity is 0.1 fmol/tube, and the standard concentration that displaces 50% of tracer is 5 fmol/tube.

B. Binding of Compounds of SEQ ID NO: 1 or Derivatives Thereof to Cloned Receptors Expressed on COS Cells In addition to the cAMP accumulation assay described below, compounds of SEQ ID NO: 1 or derivatives thereof may also be iodinated and used in a radioreceptor-based assay in transiently transfected COS cells. COS-7 cells are grown in 15 cm plates in DMEM, 10% heat-inactivated FBS, 10 mg/L gentamycin until 80–90% confluent. Twenty-four hours after transfection by the DEAE/Dextran method (Sambrook et al., supra), with 1–2 μg of plasmid DNA, the cells are trypsinized and replated in multiwell plastic dishes (16 or 35 mm diameter, Costar, Cambridge, Mass.) at a cell concentration of $5 \times 10^4$ cells/cm$^2$. Cell number increased only slightly after transfection. After continuing culture for another 48 h, radioreceptor assays are performed. The culture medium is replaced with buffer containing 50 mM Tris-HCL (pH 7.7), 100 mM NaCl, 2 mM CaCl$_2$, 5 mM KCL, 0.5% heat-inactivated fetal bovine serum (GIBCO), and 5% heat-inactivated horse serum (KC Biological Inc., Lenexa, Kans.) immediately before studies are initiated. Unless otherwise indicated, studies are conducted with cells incubated in this buffer at 15° C. for 4 h with $4 \times 10^5$ cpm/ml ($9.6 \times 10^{-11}$ M) of $^{25}$I-labeled [Ala$^1$]PTH(1–14) amide or $^{25}$I-labeled [Nle$^8$]PTH(1–14).

III. Vectors, Host Cells, and Recombinant Expression

The present invention also relates to vectors that comprise a polynucleotide of the present invention, and host cells which are genetically engineered with vectors of the invention and the production of polypeptides of the invention by recombinant techniques. Cell-free translation systems can also be employed to produce such proteins using RNAs derived from the DNA constructs of present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., Molecular Cloning: A Laboratory Manual (supra).

RNA vectors may also be utilized for the expression of the nucleic acids encoding compounds of SEQ ID NO: 1 or derivatives thereof disclosed in this invention. These vectors are based on positive or negative strand RNA viruses that naturally replicate in a wide variety of eukaryotic cells (Bredenbeek, P. J. & Rice, C. M., Virology 3: 297–310, 1992). Unlike retroviruses, these viruses lack an intermediate DNA life-cycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., TIBTECH 11:18–22, 1993; Frolov, I., et al, Proc. Natl. Acad. Sci. (USA) 93: 11371–11377,1996). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

For secretion of the translated protein into the lumen of the endoplasmic reticulum, into the periplasmic space or into the extracellular environment appropriate secretion signals may be incorporated into the desired polypeptide. These signals may be endogenous to the polypeptide or they may be heterologous signals.

The expression of a DNA sequence requires that the DNA sequence be "operably linked" to DNA sequences which contain transcriptional and translational regulatory information. An operable linkage is a linkage in which the control or regulatory DNA sequences and the DNA sequence sought to be expressed are connected in such a way as to permit gene expression. The precise nature of the "control regions" needed for gene expression may vary from organism to organism, but shall in general include a promoter region which, in prokaryotic cells, contains both the promoter (which directs the initiation of RNA transcription) as well as DNA sequences which, when transcribed into RNA, will signal the initiation of protein synthesis. Regulatory regions in eukaryotic cells will in general include a promoter region sufficient to direct the initiation of RNA synthesis.

Two DNA sequences are said to be operably linked if the nature of the linkage between the two DNA sequences does not (1) result in the introduction of a frameshift mutation, (2) interfere with the ability of the promoter region sequence to direct the transcription of the fusion protein-encoding sequence or (3) interfere with the ability of the fusion protein-encoding sequence to be transcribed by the promoter region sequence. Thus, a promoter region would be operably linked to a DNA sequence if the promoter were capable of transcribing that DNA sequence.

The joining of various DNA fragments, to produce the expression vectors of this invention is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligates. In the case of a fusion protein, the genetic construct encodes an inducible promoter which is operably linked to the 5' gene sequence of the fusion protein to allow efficient expression of the fusion protein.

To express compounds of SEQ ID NO: 1 or a derivative thereof in a prokaryotic cell (such as, for example, E. coli, B. subtilis, Pseudomonas, Streptomyces, etc.), it is necessary to operably link the SEQ ID NO: 1-encoding DNA sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pBR325, etc. Examples of inducible prokaryotic promoters include the major right and left promoters of bacteriophage λ, (PL and PR), the trp, recA. lacZ. lacI. and gal promoters of E. coli, the α-amylase (Ulmanen, I. et al., J. Bacteriol. 162:176–182 (1985)), and the o-28-specific promoters of B. subtilis (Gilman, M. Z. et al., Gene 32:11–20 (1984)), the promoters of the bacteriophages of Bacillius (Gryczan, T. J., In. The Molecular Biology of the Bacilli, Academic Press, Inc., New York (1982)), and Streptomyces promoters (Ward, J. M. et al., Mol. Gen. Genet. 203:468–478 (1986)). Prokaryotic promoters are reviewed by Glick, B. R., J. Ind. Microbiol. 1:277–282 (1987); Cenatiempo, Y., Biochimie 68:505–516 (1986)); and Gottesman, S., Ann. Rev. Genet. 18:415–442 (1984)).

The preferred prokaryotic promoter for this invention is the E. coli trp promoter, which is inducible with indole acrylic acid.

If expression is desired in a eukaryotic cell, such as yeast, fungi, mammalian cells, or plant cells, then it is necessary to employ a promoter capable of directing transcription in such a eukaryotic host. Preferred eukaryotic promoters include the promoter of the mouse metallothionein I gene (Hamer, D. et al., J. Mol. Appl. Gen. 1:273–288 (1982)); the TK promoter of Herpes virus (McKnight, S., Cell 31:355–365 (1982)); the SV40 early promoter (Benoist, C., et al., Nature (London) 290:304–310 (1981)); and the yeast ga 14 gene promoter (Johnston, S. A., et al., Proc. Natl. Acad. Sci. (USA) 79:6971–6975 (1982); Silver, P. A., et al., Proc. Natl. Acad. Sci. (USA) 81:5951–5955 (1984)).

Preferably, the introduced gene sequence will be incorporated into a plasmid or viral vector capable of autonomous replication in the recipient host. Any of a wide variety of vectors may employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in E. coli (such as, for example, pBR322, ColEl, pSC101, pACYC184, πVX. Such plasmids are, for example, disclosed by Maniatis, T., et al., In: Molecular Cloning, A Laboratory Manual, Cold Spring Harbor Press, Cold Spring Harbor, N.Y. (1982)). Preferred plasmid expression vectors include the pGFP-1 plasmid described in Gardella et al., J. Biol. Chem. 265:15854–15859 (1989), or a modified plasmid based upon one of the pET vectors described by Studier and Dunn, Methods in Enzymology 185:60–89 (1990). Bacillus plasmids include pC194, pC221, pT127, etc. Such plasmids are disclosed by Gryczan, T. In: The Molecular Biology of the Bacilli, Academic Press, NY pp. 307–329 (1982). Suitable Streptomyces plasmids include pIJIOI (Kendall, K. J. et al., J. Bacteriol. 169:4177–4183 (1987)), and streptomyces bacteriophages such as φC31 (Chater, K. F. et al., In: Sixth International Symposium on Actinomycetales Biology, Akademiai Kaido, Budapest, Hungary, pp.45–54 (1986)). Pseudomonas plasmids are reviewed by John, J. F. et al., Rev. Infect. Dis. 8:693–704 (1986)), and Izaki, K., Jon. J Bacteriol. 33:729–742 (1978)).

Preferred eukaryotic expression vectors include, without limitation, BPV, vaccinia, 2-micron circle etc. Such expression vectors are well known in the art (Botstein, D., et al., Miami Wntr. Symp. 19:265–274 (1982); Broach, J. R., In: The Molecular Biology of the Yeast Saccharomyces: Life Cycle and Inheritance, Cold Spring Harbor Laboratory, Cold Spring Harbor, N.Y. pp. 445–470 (1981); Broach, J. R., Cell 28:203–204 (1982); Bollon, D. P., et al., J. Clin. Hematol. Oncol. 10:39–48 (1980); Maniatis, T., In: Cell Biology: A Comprehensive Treatise, Vol. 3, Gene Expression, Academic Press, N.Y., pp. 563–608 (1980)).

In addition to microorganisms, cultures of cells derived from multicellular organisms may also be used as hosts. In principle, any such cell culture is workable, whether from vertebrate or invertebrate cellular sources. Interest, however, has been greater with cells from vertebrate sources. Examples of useful vertebrate host cell lines are VERO and HeLa cells, Chinese hamster ovary (CHO) cell lines, W138, BHK, COS-7, and MDCKcell lines. Expression vectors for such cells ordinarily include (if necessary) an origin of replication, a promoter located in front of or upstream to the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Simian Virus 40 (SV40) and cytomegalovirus. The early and late promoters of SV40 virus are particularly useful because both are obtained easily from the virus as a fragment which also contains the SV40 vial origin of replication (Fiers et al., Nature 273:113 (1978)).

An origin of replication may be provided either by construction of the vector to include an exogenous origin, such as may be derived from SV40 or other viral (e.g. Polyoma, Adeno, VSV, BPV) source or may be provided by the host cell chromosomal replication mechanism. If the vector is integrated into the host cell chromosome, the latter is often sufficient.

If cells without formidable cell membrane barriers are used as host cells, transfection is carried out by the calcium phosphate precipitation method as described by Graham and Van der Erb, Virology 52:546 (1978). However, other methods for introducing DNA into cells, such as by nuclear injection or by protoplast fusion may also be used. In the case of gene therapy, the direct naked plasmid or viral DNA injection method, with or without transfection-facilitating agents such as, without limitation, liposomes, provides an alternative approach to the current methods of in vivo or in vitro transfection of mammalian cells. If prokaryotic cells or cells which contain substantial cell wall constructions are used, the preferred method oftransfection is calcium treatment, using calcium chloride as described in Cohen et al., *Proc. Natl. Acad Sci. USA* 69:2110 (1972).

IV. Utility and Administration of Compounds of SEQ ID NO:1 or Derivatives Thereof Compounds of SEQ ID NO: 1 or derivatives thereof of this invention are useful for the prevention and treatment of a variety of mammalian conditions manifested by loss of bone mass. In particular, the compounds of this invention are indicated for the prophylaxis and therapeutic treatment of osteoporosis and osteopenia in humans. Furthermore, the compounds of this invention are indicated for the prophylaxis and therapeutic treatment of other bone diseases. The compounds of this invention are indicated for the prophylaxis and therapeutic treatment of hypoparathyroidism. Finally, the compounds of this invention are indicated for use as agonists for fracture repair and as antagonists for hypercalcemia.

In general, compounds of SEQ ID NO: 1 or derivatives thereof of this invention, or salts thereof, are administered in amounts between about 0.01 and 1 $\mu$g/kg body weight per day, preferably from about 0.07 to about 0.2 $\mu$g/kg body weight per day. For a 50 kg human female subject, the daily dose of biologically active compounds of SEQ ID NO: 1 or derivatives thereof is from about 0.5 to about 50 $\mu$gs, preferably from about 3.5 to about 10 $\mu$gs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. For example, this dosage may be delivered in a conventional pharmaceutical composition by nasal insufflation.

The selection of the exact dose and composition and the most appropriate delivery regimen will be influenced by, inter alia, the pharmacological properties of the selected compounds of SEQ ID NO: 1 or derivatives thereof, the nature and severity of the condition being treated, and the physical condition and mental acuity of the recipient.

Representative preferred delivery regimens include, without limitation, oral, parenteral (including subcutaneous, transcutaneous, intramuscular and intravenous), rectal, buccal (including sublingual), transdermal, and intranasal insufflation.

Pharmaceutically acceptable salts retain the desired biological activity of the compounds of SEQ ID NO: 1 or derivatives thereof without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like.

A further aspect of the present invention relates to pharmaceutical compositions comprising as an active ingredient compounds of SEQ ID NO: 1 or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for the most preferred route of administration, nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189, incorporated by reference herein. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987, incorporated by reference herein.

Like PTH, the PTH variants may be administered in combination with other agents useful in treating a given clinical condition. When treating osteoporosis and other bone-related disorders for example, the PTH variants may be administered in conjunction with a dietary calcium supplement or with a vitamin D analog (see U.S. Pat. No. 4,698,328). Alternatively, the PTH variant may be administered, preferably using a cyclic therapeutic regimen, in combination with bisphosphonates, as described for example in U.S. Pat. No. 4,761,406, or in combination with one or more bone therapeutic agents such as, without limitation, calcitonin and estrogen.

V. Receptor-Signaling Activities of Compounds of SEQ ID NO: 1 or Derivatives Thereof A crucial step in the expression of hormonal action is the interaction of hormones with receptors on the plasma membrane surface of target cells. The formation of hormone-receptor complexes allows the transduction of extracellular signals into the cell to elicit a variety of biological responses.
A. Screeningfor PTH-1 Receptor Antagonists and Agonists Polypeptides of the invention may be screened for their agonistic or antagonistic properties using the cAMP accumulation assay. Cells expressing PTH-1 receptor on the cell surface are incubated with native PTH(1–84) for 5–60 minutes at 37° C., in the presence of2 mM IBMX (3-isobutyl-1-methyl-xanthine, Sigma, St. Louis, Mo.). Cyclic AMP accumulation is measured by specific radio-immunoassay, as described above. A compound of SEQ ID NO: 1 or a derivative thereofthat competes with native PTH(1–84) for binding to the PTH-1 receptor, and that inhibits the effect of native PTH(1–84) on cAMP accumulation, is considered a competitive antagonist. Such a compound would be useful for treating hypercalcemia.

Conversely, a compound of SEQ ID NO: 1 or a derivative thereof that does not compete with native PTH(1–84) for binding to the PTH-1 receptor, but which still prevents native PTH(1–84) activation of cAMP accumulation (presumably by blocking the receptor activation site) is considered a non-competitive antagonist. Such a compound would be useful for treating hypercalcemia.

A compound of SEQ ID NO: 1 or a derivative thereof that competes with native PTH(1–84) for binding to the PTH-1 receptor, and which stimulates cAMP accumulation in the presence or absence of native PTH(1–84) is a competitive agonist. A compound of SEQ ID NO: 1 or a derivative thereof that does not compete with native PTH(1–84) for binding to the PTH-1 receptor but which is still capable of stimulating cAMP accumulation in the presence or absence of native PTH(1–84), or which stimulates a higher cAMP accumulation than that observed by a compound of SEQ ID NO: 1 or a derivative thereof alone, would be considered a non-competitive agonist.

VI. Therapeutic Uses of Compounds of SEQ ID NO: 1 or Derivatives Thereof

Some forms of hypercalcemia and hypocalcemia are related to the interaction between PTH and PTHRP and the PTH-1 and PTH-2 receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypernephroma. Hypocalcemia, a condition in which the serum calcium level is abnormally low, may result from a deficiency of effective PTH, e.g., following thyroid surgery.

Nucleic acids of the invention which encode compounds of SEQ ID NO: 1 or derivatives thereof may also be linked to a selected tissue-specific promoter and/or enhancer and the resultant hybrid gene introduced, by standard methods (e.g., as described by Leder et al., U.S. Pat. No. 4,736,866, herein incorporated by reference), into an animal embryo at an early developmental stage (e.g., the fertilized oocyte stage), to produce a transgenic animal which expresses elevated levels of compounds of SEQ ID NO: 1 or derivatives thereof in selected tissues (e.g., the osteocalcin promoter for bone). Such promoters are used to direct tissue-specific expression of compounds of SEQ ID NO: 1 or derivatives thereof in the transgenic animal.

In addition, any other amino-acid substitutions of a nature, which do not destroy the ability of the PTH/PTHrP analog to antagonize or agonize the PTH-1/PTH-2 receptor (as determined by assays known to the skilled artisan and discussed below), are included in the scope of the present invention.

By "agonist" is intended a ligand capable of enhancing or potentiating a cellular response mediated by the PTH-1 receptor. By "antagonist" is intended a ligand capable of inhibiting a cellular response mediated by the PTH-1 receptor. Whether any candidate "agonist" or "antagonist" of the present invention can enhance or inhibit such a cellular response can be determined using art-known protein ligand/receptor cellular response or binding assays, including those described elsewhere in this application.

In accordance with yet a further aspect of the invention, there is provided a method for treating a medical disorder that results from altered or excessive action of the PTH-1 receptor, comprising administering to a patient a therapeutically effective amount of a compound of SEQ ID NO: 1 or a derivative thereof sufficient to inhibit activation of the PTH- 1 receptor of said patient.

In this embodiment, a patient who is suspected of having a disorder resulting from altered action of the PTH-1 receptor may be treated using compounds of SEQ ID NO: 1 or derivatives thereof of the invention which are a selective antagonists of the PTH-1 receptor. Such antagonists include compounds of SEQ ID NO: 1 or derivatives thereof of the invention which have been determined (by the assays described herein) to interfere with PTH-1 receptor-mediated cell activation or other derivatives having similar properties.

To administer the antagonist, the appropriate compound of SEQ ID NO: 1 or a derivative thereof is used in the manufacture of a medicament, generally by being formulated in an appropriate carrier or excipient such as, e.g., physiological saline, and preferably administered intravenously, intramuscularly, subcutaneously, orally, or intranasally, at a dosage that provides adequate inhibition of a compound of SEQ ID NO: 1 or a derivative thereof binding to the PTH-1 receptor. Typical dosage would be 1 ng to 10 mg of the peptide per kg body weight per day.

In a preferred embodiment, the compound of SEQ ID NO: 1 or a derivative thereofused in the method has a single amino acid deletion at the amino terminus. In this preferred embodiment, the PTH/PTHrP analog is PTH(2–14)/PTHrP (2–14). In yet another preferred embodiment, the compound of SEQ ID NO: 1 or a derivative thereof used in the method has a two amino acid deletion at the amino terminus. In this preferred embodiment, the PTH/PTHrP analog is PTH (3–14)/PTHrP(3–14).

In accordance with yet a further aspect of the invention, there is provided a method for treating osteoporosis, comprising administering to a patient a therapeutically effective amount of a compound of SEQ ID NO: 1 or a derivative thereof, sufficient to activate the PTH-1 receptor of said patient. Similar dosages and administration as described above for the PTH/PTHrP antagonist, may be used for administration of a PTH/PTHrP agonist, e.g., for treatment of conditions such as osteoporosis, other metabolic bone disorders, and hypoparathyroidism and related disorders.

In a preferred embodiment, the compound of SEQ ID NO: 1 or a derivative thereof used in the method has an amino acid substitution of alanine for serine at amino acid position 1 of compound of SEQ ID NO: 1. In this particular embodiment, the PTH derivative is [Ala$^1$]PTH(1–4)(SEQ ID NO: 5). In another preferred embodiment, the compound of SEQ ID NO: 1 or a derivative thereof used in the method has an amino acid substitution of histidine for isoleucine at position 5 of SEQ ID NO: 1. In this particular embodiment, the PTHrP derivative is [Ile$^5$] PTHrP(1–14). (SEQ ID NO: 2)

It will be appreciated to those skilled in the art that the invention can be performed within a wide range of equivalent parameters of composition, concentration, modes of administration, and conditions without departing from the spirit or scope of the invention or any embodiment thereof.

Having now fully described the invention, the same will be more readily understood by reference to specific examples which are provided by way of illustration, and are not intended to be limiting of the invention, unless herein specified.

EXAMPLE 1

To begin to identify the minimum length required for bioactivity of PTH and PTHrP, the inventors constructed synthetic peptides based upon the first 14 amino acids of native human PTH. As a first step towards optimization the inventors replaced the serine at position one by alanine; this substitution, which corresponds to the amino acid found at position I in rat and bovine PTH, as well as in all PTHrP molecules reported so far (human, bovine, dog, rat, mouse, chicken), results in a measurable increase in bioactivity over the background level of bioactivity of the native PTH(1–14) peptide. The C-terrninal residue of this new peptide, herein called [Ala$^1$] PTH(1–14), is arnidated.

The ability of [Ala$^1$] PTH(1–14) to stimulate cAMP formation in COS-7 cells expressing the cloned human PTH-1 receptor is shown in FIG. 1. A small cAMP response can be seen even with the shorter peptide [Ala$^1$] PTH(1–9).

As expected, the carboxy-terrninal fragment PTH(15–31) was inactive (FIG. 1). Each of these peptides was inactive in control COS-7 cells transected with a DNA vector lacking the PTH-1 receptor gene.

Figure 4:
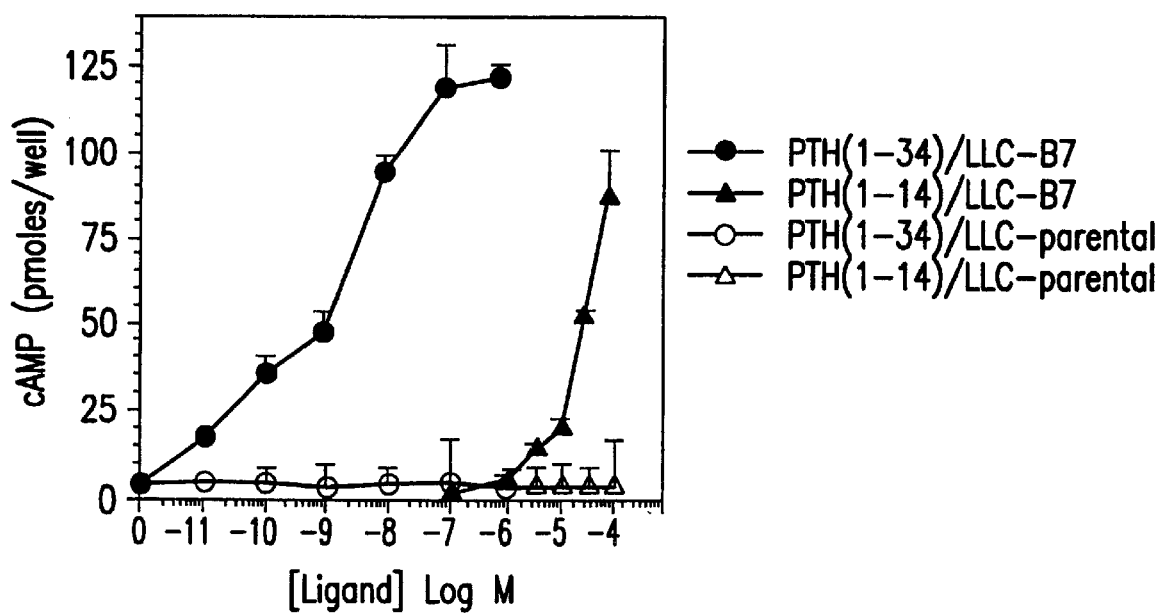
FIG. 4. cAMP dose response curves of PTH(1–14) in LLC-B7 cells and in untransfected LLC-PK1 cells. PTH (1–14) and PTH(1–34) control peptides were tested as in FIG. 3. As can be seen, the response to PTH(1–14) in these cells is completely dependent on the presence of the PTH-1 receptor.
Figure 5:
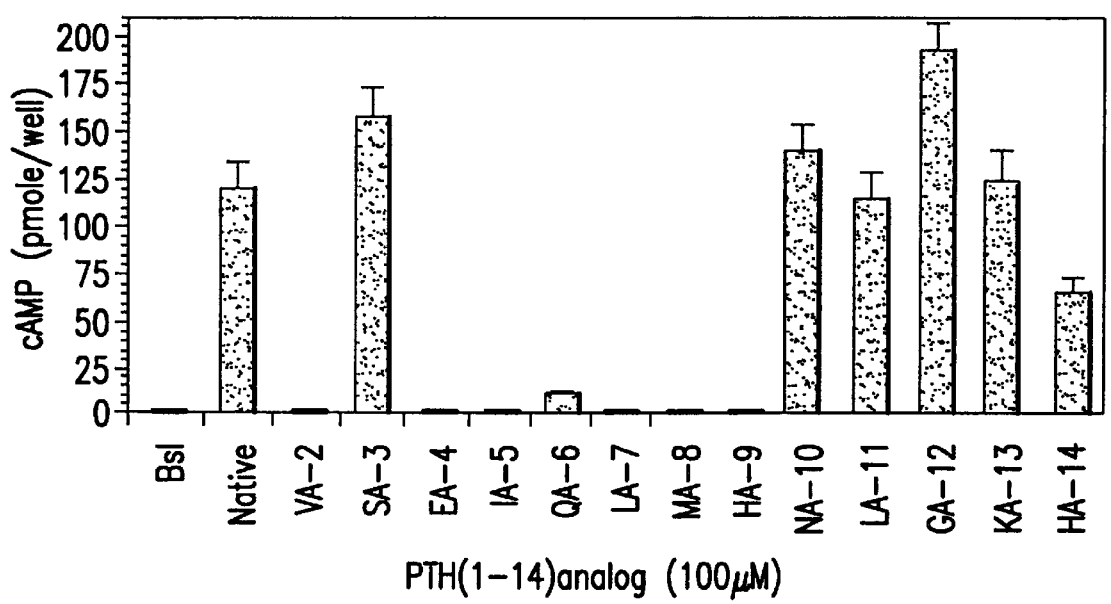
FIG. 5. Alanine-scan of PTH(1–14) in LLC-B7 cells. Each PTH(1–14) was tested in duplicate at a dose of 100 $\mu$M. LLC-B7 cells in 24 plates were treated with the indicated peptides, for 60 mins at 21° C., and then intracellular cAMP levels were measured.
Figure 6A:
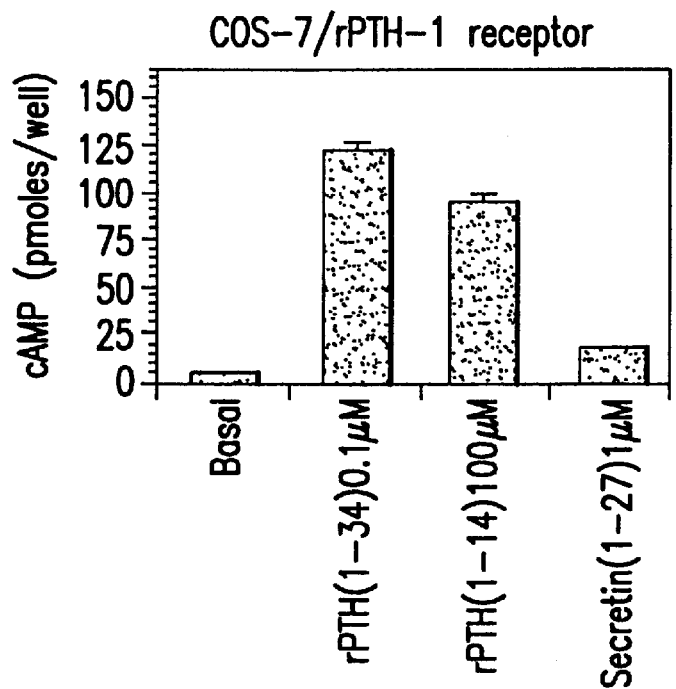
FIG. 6. Specificity of PTH(1–14). The analog PTH(1–14) was tested in COS-7 cells transfected with rat secretin receptor, which responds fully to the control native secretin (1–27). PTH(1–14) does not stimulate cAMP in these cells. Thus, the response to PTH(1–14) is dependent on the presence of the PTH-1 receptor.
Figure 6B:
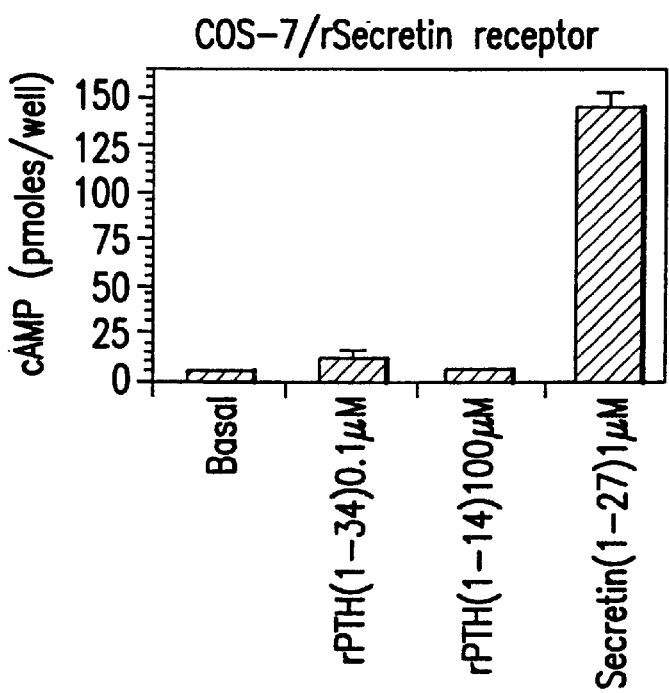

To demonstrate PTH(1–14) specificity, its ability to stimulate cAMP production in COS-7 cells transfected with the rat secretin receptor (rSR)—a related Family B receptor that does not bind or respond to PTH was tested. As shown in the FIG. 6, PTH(1–14) is inactive in cells expressing rSR. Thus, the response to PTH(1–14) in COS-7 cells is dependent on PTH-1 receptor expression. PTH(1–14) specificity was also tested using the porcine renal cell line LLC-PK1, either untransfected or stably transfected with the human PTH-1 receptor, the LLC-B7 cell line. FIG. 4 shows that the PTH(1–14) response in these cells is dependent on PTH-1 receptor expression.

EXAMPLE 2

Figure 2:
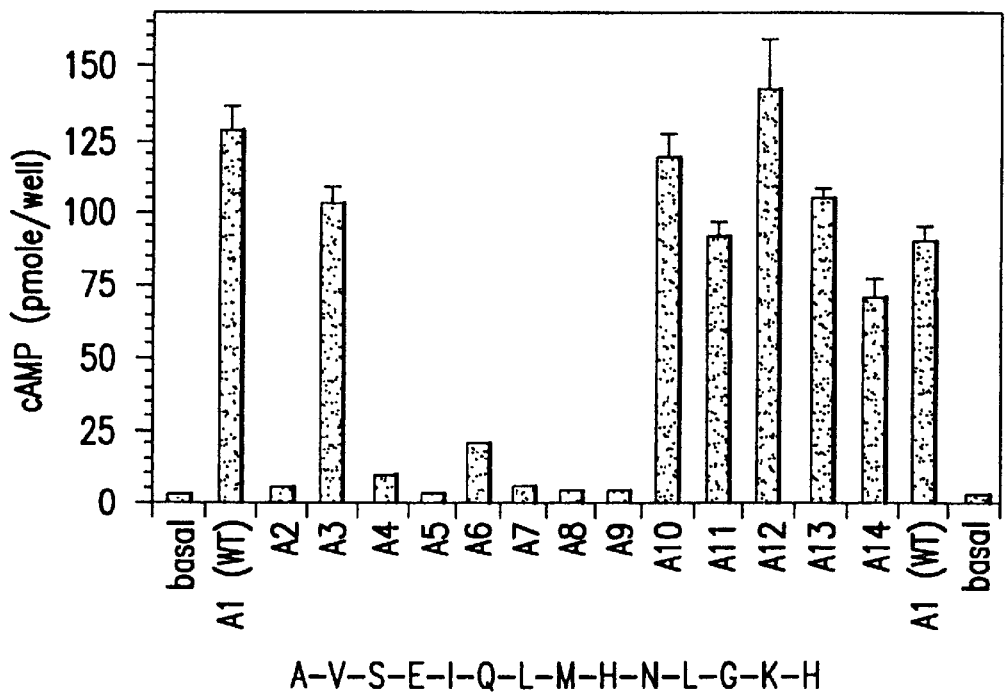
FIG. 2. Alanine-scan of PTH(1–14). Shown are the bioactivities of 14 different PTH(1–14) derivatives, each having a different amino acid of the native sequence (shown at bottom of figure) replaced by alanine. Peptides were chemically synthesized, purified and tested for ability to stimulate cAMP formation in COS-7 cells expressing the cloned human PTH-1 receptor. Peptides were tested in duplicate (±s.e.m.) at a dose of 67 $\mu$M. As a control, untreated cells, indicated by basal, were measured. The PTH(1–14) containing alanine at position 1 was used as the wild-type reference. Cells were stimulated for 30 minutes at 21° C.
Figure 3:
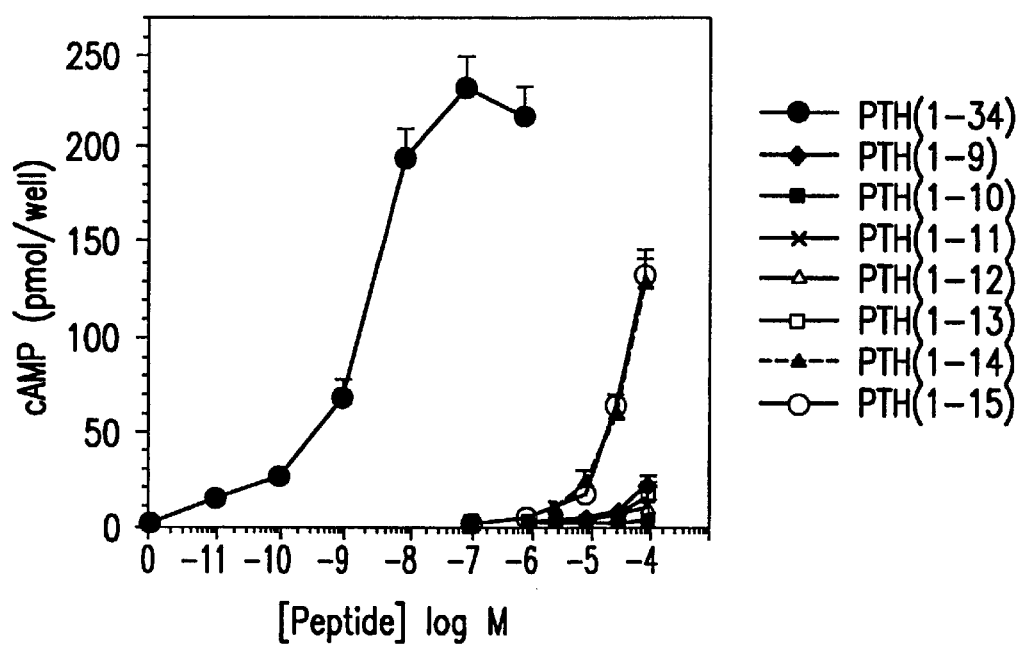
FIG. 3. cAMP dose response curves of short amino-terminal PTH analogs in LLC-PK1 cells stably transfected with the human PTH-1 receptor (LLC-B7 cells). LLC-B7 cells in 24 plates were treated with the indicated peptides for 60 mins at 21° C., and then intracellular cAMP levels were measured. All PTH peptides shown are based on the rat PTH sequence and are carboxy-terminally amidated. As can be seen, there is no gain in activity when the PTH(1–14) peptide is extended to residue 15; and PTH(1–13) or shorter analogs exhibit only very weak activity.

As noted above in Example 1, even with the Ser1→Ala substitution, the [Ala$^1$] PTH(1–14) peptide is weaker than native PTH(1–34) (FIG. 1). Thus, additional optimization of the [Ala$^1$] PTH(1–14) sequence to improve potency and efficacy was pursued. As part of this optimization process, an alanine-scan of the native PTH(1–14) sequence was performed. In this study, 14 different peptides were synthesized, each 14 amino acids in length and differing from each other by having one native amino acid replaced with alanine. This alanine-scan permits the classification of each individual residue in the native 1–14 sequence as either critical for function (intolerant) or not critical for function (tolerant). The tolerant residues reside in one well-defined carboxy-terminal segment that extends from Asn-10 to His-14, whereas the intolerant residues fall within the Ala-1 to His-9 segment (FIG. 2). Note that Ala-1 and Ser-3 were not adequately tested in this study, since position 1 is alanine in the native rat and bovine sequences, and Ser→Ala at position 3 is a conservative substitution. For example, as predicted from the alanine-scan results, the [Ala$^1$] PTH(1–9) fragment, which contains all of the intolerant residues, exhibits some biological activity (FIG. 1).

EXAMPLE 3

Figure 7:
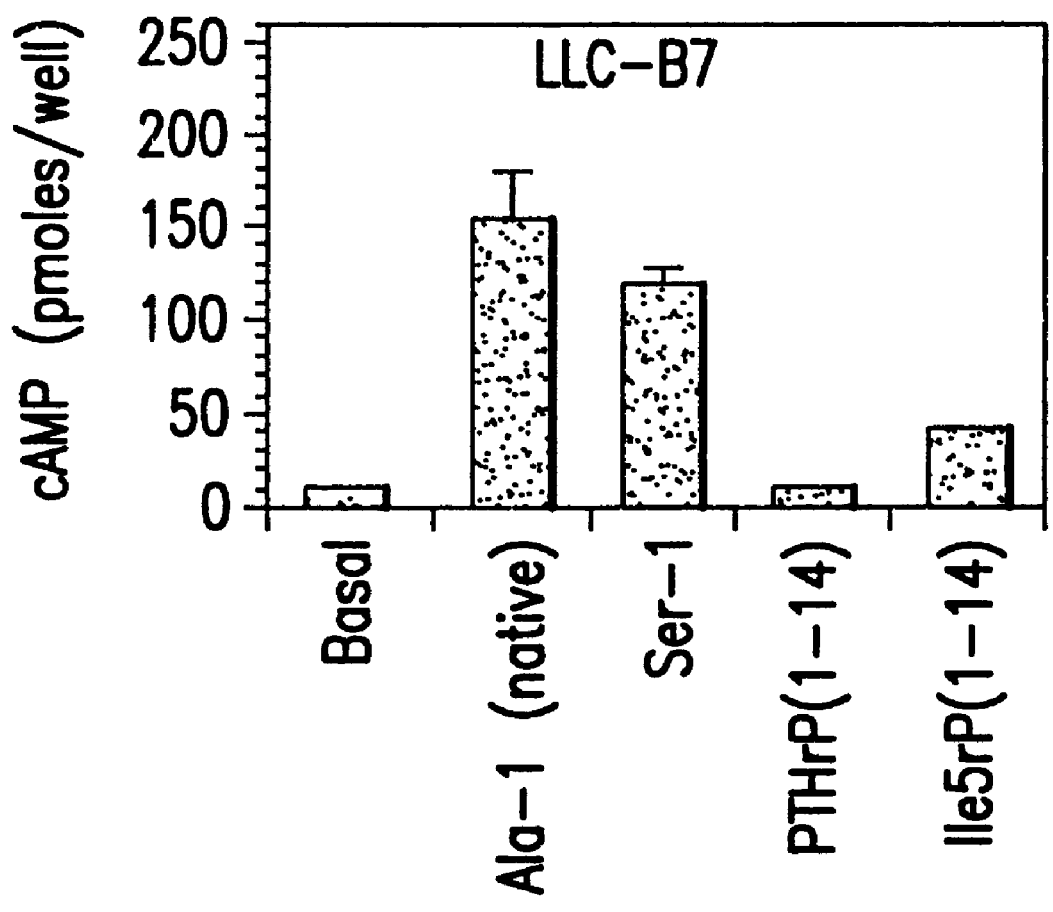
FIG. 7. cAMP activity of [Ile5]PTHrP(1–14). LLC-B7 cells were treated with the indicated peptide ligand, each at 100 $\mu$M, and then intracellular cAMP levels were measured.

The analysis extends to the PTHrP(1–14) sequence as well. The inventors found that one monosubstitution, which replaces histidine at the critical 5 position in PTHrP(1–14) with isoleucine. Thus, in this particular embodiment, the pTHrP analog is [Ile$^5$] PTHrP(1–14). FIG. 7. shows the cAMP activity results obtained with [Ile5]PTHrP(1–14). LLC-B7 cells were treated with the indicated peptide ligand, each at 100 µM, and then intracellular cAMP levels were measured. Substitution of isoleucine with histidine at the critical 5 position of PTHrP results in a new analog with enhanced potency, relative to native PTHrP(1–14).

What is claimed is:

1. A biologically active peptide consisting of the formula:
   (a) $X_{01}$ValSerGlu$X_{02}$GlnLeu$X_{03}$His$X_{04}$$X_{05}$GlyLys$X_{06}$ (SEQ ID NO: 1);
   (b) fragments containing amino acids 1–11, 1–12, or 1–13 of SEQ ID. NO: 1;
   (c) pharmaceutically acceptable salts thereof; or
   (d) N- or C-derivatives;
   wherein:
   $X_{01}$ is Ser or Ala;
   $X_{02}$ is Ile or His;
   $X_{03}$ is Met, Leu or Nle;
   $X_{04}$ is Asn or Asp;
   $X_{05}$ is Leu or Lys; and
   $X_{06}$ is His or Ser,
   provided that said peptide in not PTHrP (1–14)SEQ ID NO: 4.

2. The peptide of claim 1 AlaValSerGluIleGlnLeuMetHisAsnLeuGlyLysHis (SEQ ID NO: 5).

3. The peptide of claim 1 wherein the peptide is labeled with a label selected from the group consisting of a radio label, a fluorescent label, a bioluminescent label, and a chemiluminescent label.

4. A The peptide of claim 3, wherein said radio label is $^{99m}$Tc.

5. A method for treating mammalian conditions characterized by decreases in bone mass, which method comprises administering to a subject in need thereof an effective bone mass-increasing amount of the biologically active peptide of claim 1 and a pharmaceutically acceptable carrier.

6. The method of claim 5, wherein the condition to be treated is osteoporosis.

7. The method of claim 5, wherein said osteoporosis is old age osteoporosis.

8. The method of claim 5, wherein said osteoporosis is post-menopausal osteoporosis.

9. The method of claim 5, wherein the effective amount of said peptide for increasing bone mass is from about 0.01 µg/kg/day to about 1.0 µg/kg/day.

10. The method of claim 5, wherein the method of administration is parenteral.

11. The method of claim 5, wherein the method of administration is subcutaneous.

12. The method of claim 5, wherein the method of administration is nasal insufflation.

13. A pharmaceutical composition comprising:

(a) a biologically active peptide consisting of the formula SerValSerGluIleGlnLeuMetHisAsnLeuGlyLysHis (SEQ ID NO: 3);
(b) fragments thereof containing amino acids 1–11, 1–12, or 1–13 of SEQ. ID. NO: 3;
(c) pharmaceutically acceptable salts thereof; or
(d) N- or C-derivatives thereof; and a pharmaceutically acceptable carrier.

14. A method for treating mammalian conditions characterized by decreases in bone mass, which method comprises administering to a subject in need thereof an effective bone mass-increasing amount of the biologically active peptide of claim 13 and a pharmaceutically acceptable carrier.

15. A pharmaceutical composition comprising:
(a) a biologically active peptide consisting of the formula AlaValSerGluHisGlnLeuLeuHisAspLysGlyLysSer (SEQ ID NO: 4);
(b) fragments thereof containing amino acids 1–9, 1–10, 1–11, 1–12, or 1–13 of SEQ. ID. NO: 4;
(c) pharmaceutically acceptable salts thereof; or
(d) N- or C-derivatives thereof and a pharmaceutically acceptable carrier.

16. A method for treating mammalian conditions characterized by decreases in bone mass, which method comprises administering to a subject in need thereof an effective bone mass-increasing amount of the biologically active peptide of claim 15 and a pharmaceutically acceptable carrier.

* * * * *

SEQUENCE LISTING

<160> NUMBER OF SEQ ID NOS: 13

<210> SEQ ID NO 1
<211> LENGTH: 14
<212> TYPE: PRT
<213> ORGANISM: Artificial Sequence
<220> FEATURE:

```
<221> NAME/KEY: UNSURE
<222> LOCATION: (1)
<223> OTHER INFORMATION: Amino acid may be Ser or Ala
<220> FEATURE:
<221> NAME/KEY: UNSURE
<222> LOCATION: (5)
<223> OTHER INFORMATION: Amino acid may be Ile or His
<220> FEATURE:
<221> NAME/KEY: UNSURE
<222> LOCATION: (8)
<223> OTHER INFORMATION: Amino acid may be Met, Leu or Nle
<220> FEATURE:
<221> NAME/KEY: UNSURE
<222> LOCATION: (10)
<223> OTHER INFORMATION: Amino acid may be Asn or Asp
<220> FEATURE:
<221> NAME/KEY: UNSURE
<222> LOCATION: (11)
<223> OTHER INFORMATION: Amino acid may be Leu or Lys
<220> FEATURE:
<221> NAME/KEY: UNSURE
<222> LOCATION: (14)
<223> OTHER INFORMATION: Amino acid may be His or Ser
<220> FEATURE:
<223> OTHER INFORMATION: Description of Artificial Sequence: synthetic
      peptide

<400> SEQUENCE: 1

Xaa Val Ser Glu Xaa Gln Leu Xaa His Xaa Xaa Gly Lys Xaa
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Ala Val Ser Glu Ile Gln Leu Leu His Asp Lys Gly Lys Ser
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Ser Val Ser Glu Ile Gln Leu Met His Asn Leu Gly Lys His
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Ala Val Ser Glu His Gln Leu Leu His Asp Lys Gly Lys Ser
 1               5                  10

<210> SEQ ID NO 5
<211> LENGTH: 14
<212> TYPE: PRT
<213> ORGANISM: Artificial Sequence
```

```
<220> FEATURE:
<223> OTHER INFORMATION: Description of Artificial Sequence: synthetic
      peptide

<400> SEQUENCE: 5

Ala Val Ser Glu Ile Gln Leu Met His Asn Leu Gly Lys His
 1               5                  10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Ala Val Ser Glu Ile Gln Leu Met His
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Ala Val Ser Glu Ile Gln Leu Leu His
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Ala Val Ser Glu His Gln Leu Leu His
 1               5

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Ser Val Ser Glu His Gln Leu Leu His Asp Lys Gly Lys Ser
 1               5                  10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

Ser Val Ser Glu His Gln Leu Leu His
 1               5
```

```
<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Val Ser Glu Ile Gln Leu Met His Asn Leu Gly Lys His
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Val Ser Glu Ile Gln Leu Leu His Asp Lys Gly Lys Ser
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Val Ser Glu His Gln Leu Leu His Asp Lys Gly Lys Ser
 1               5                  10
```